United States Patent [19]

Smutek et al.

[11] Patent Number: 4,560,796
[45] Date of Patent: Dec. 24, 1985

[54] PROCESS FOR THE MODIFICATION OF THE CRYSTAL FORM OF DICYANDIAMIDE

[75] Inventors: Gerhard Smutek, Tacherting; Hermann Raveling, Altenmarkt, both of Fed. Rep. of Germany

[73] Assignee: SKW Trostberg Aktiengesellschaft, Trostberg, Fed. Rep. of Germany

[21] Appl. No.: 547,673

[22] Filed: Nov. 1, 1983

[30] Foreign Application Priority Data

Nov. 6, 1982 [DE] Fed. Rep. of Germany ....... 3241070

[51] Int. Cl.⁴ ............................................. C07C 129/14
[52] U.S. Cl. ..................................................... 564/104
[58] Field of Search ........................................... 564/104

[56] References Cited

U.S. PATENT DOCUMENTS 3,308,022  3/1967  Cummings et al. .................. 424/326

FOREIGN PATENT DOCUMENTS 3147821  6/1983  Fed. Rep. of Germany .
48-56625  8/1973  Japan .
157023  12/1977  Japan .

*Primary Examiner*—Charles F. Warren
*Assistant Examiner*—R. A. Picard
*Attorney, Agent, or Firm*—Felfe & Lynch

[57] ABSTRACT

The present invention provides a process for the modification of the crystal form of dicyandiamide, wherein dicyandiamide is crystallized from aqueous solution in the presence of 0.001 to 10% by weight of polyvinyl alcohol and/or of a water-soluble cellulose ether derivative, referred to the amount of dicyandiamide. The crystalline dicyandiamide obtained in this manner has outstanding flow and storage properties and its mechanical strength is substantially improved.

11 Claims, No Drawings

PROCESS FOR THE MODIFICATION OF THE CRYSTAL FORM OF DICYANDIAMIDE

The present invention is concerned with a process for the modification of the crystal form of dicyandiamide.

Dicyandiamide is an important technical product with a large number of uses. In particular, it is used as an intermediate for the production of melamine, guanamines and guanidine derivatives, as well as for the synthesis of pharmaceuticals, as starting material for flame-protection agents and dicyandiamide resins which are preponderantly uses as paper, textile and dyeing adjuvants. Furthermore, dicyandiamide is used as an additive for polymeric compounds and, not least, as a nitrification inhibitor in agriculture.

A particular disadvantage in the handling of dicyandiamide is its tendency to cake, particularly when stored, which gives rise to technical problems in the case of further use. Attempts have certainly been made to solve this problem, hitherto two ways having been followed. On the other hand, attempts have been made to add anti-caking agents, for example highly dispersed silicic acid, to the dicyandiamide. However, quite apart from the cost, such additives can have a disturbing effect on the further use of the dicyandiamide because they impair the reactivity of the dicyandiamide, or they require the removal thereof from products made with dicyandiamide, making additional purification steps necessary.

A second approach for solving the caking problem is so to change the crystal form of the dicyandiamide by appropriate additives so that it no longer crystallises as thin leaflets, this being regarded as being the cause for the caking or the poor friability. German Democratic Republic Patent Specification No. 144,915 describes water-soluble urea-formaldehyde condensation products as such agents for modifying the crystal form of dicyandiamide. A disadvantage of this process is that making the condensation product requires additional operational and investment costs.

It is, therefore, an object of the present invention to provide a process for the modification of the crystal form of dicyandiamide which does not suffer from these disadvantages and so changes the crystal form of the dicyandiamide that a friable product is obtained which can be readily handled and measured.

According to the present invention, there is provided a process for the modification of dicyandiamide in its crystal form, wherein dicyandiamide is crystallised from aqueous solution in the presence of 0.001 to 10% by weight, preferably of 0.005 to 5% by weight, of polyvinyl alcohol and/or of a water-soluble cellulose ether derivative, referred to the amount of dicyandiamide.

We have, surprisingly, found that with the help of the additives to be used according to the present invention, the dicyandiamide is obtained in the form of thick, tabular to prismatic crystals or rhombohedrons, the bulk density of which is up to 2.5 times as high as in the case of normal dicyandiamide and which has an excellent friability.

According to the present invention, there can, in principle, be used all water-soluble cellulose ether derivatives, for example:

(a) non-ionic cellulose ethers, for example, methylcellulose, hydroxyethylcellulose, hydroxypropylcellulose and hydroxybutylcellulose;

(b) mixed non-ionic cellulose ethers, for example, methylhydroxyethylcellulose, methylhydroxypropylcellulose and methylhydroxybutylcellulose;

(c) ionic cellulose ethers, for example, sodium carboxymethylcellulose;

(d) ionic/non-ionic cellulose ethers, for example, carboxymethylmethylcellulose.

Methylcellulose, hydroxyethylcellulose, methylhydroxybutylcellulose and carboxymethylmethylcellulose have proved to be especially advantageous.

For the modification of the crystal form, there can also be used cellulose-like materials, for example guar, which is a galactomannan.

When the cellulose ether derivatives or the polyvinyl alcohol are used in comparatively high concentrations, foam formation may occur which can, however, be reduced to the normal amount by the appropriate addition of commercially available defoaming agents, for example modified polyols.

Instead of pure polyvinyl alcohol, use can be made of partially saponified polyvinyl acetate.

The process according to the present invention can be carried out without any problems in conventional crystallisation apparatus, for example in stirrer, circulatory or vacuum crystallisation apparatus, whereby, depending upon the crystallisation process used, rates of cooling of from 1° to 70° C. and especially of from 10° to 50° C. per hour are to be maintained in order to achieve a change in the crystal form.

The dicyandiamide hereby crystallises out in the form of thick tablets or rhombohedra or truncated bipyramides or rice-like crystals, the bulk density of which is from 300 to 800 g./liter and preferably of from 500 to 700 g./liter.

A particular advantage of the process according to the present invention is the possibility of being able to carry out this crystallisation not only in aqueous solution but also in the production of the dicyandiamide in a strongly alkaline medium, this process being suitable for technical use especially in the production of dicyandiamide. The by-products formed do not interfere with crystallization using the form-modifying additives.

Because of their particle shape, the form-modified crystals possess outstanding flow and storage properties. That crystals exhibit improved mechanical strength with regard to particle attrition and breakage, as well as improved filtration properties.

The following Examples are given for the purpose of illustrating the present invention:

EXAMPLES 1–31

The experiments described in Examples 1 to 31 were carried out in conventional crystallisation apparatus. The assessment of the crystals were carried out according to the following criteria;

++form-modified crystals in the form of rhombohedra, truncated bipyrimids and rice-like crystals +form-modified crystals in the form of thick tablets −no form-modified crystals, thin irregular platelets For the determination of the caking tendency of the dried crystals, they were placed in a test tube, closed with a Teflon stopper which was just movable and subjected to a loading of 1 kg./cm$^2$ for 3 days. Thereafter, a pointed body was introduced vertically into the sample and the weight loading measured which is necessary for covering a definite distance. The greater is this weight loading, the greater is the caking of the sample.

The results obtained from the experiments carried out are summarised in the following Tables in which the following abbreviations are used:

PVA = polyvinyl alcohol
HEC = hyroxyethylcellulose
MC = methylcellulose
MHEC = methylhydroxyethylcellulose
HPC = hydroxypropylcellulose
MHPC = methylhydroxypropylcellulose
MHBC = methylhydroxybutylcellulose
CMC = carboxymethylcellulose
CMMC = carboxymethyl-methylcellulose

TABLE 1

Rate of cooling: 10° C./hour

| experiment No. | additives | wt. % of additive | crystal form | loading (g.) |
|---|---|---|---|---|
| comparison | — | — | — | 1000 |
| 1 | PVA | 0.01 | + | 100 |
| 2 | PVA | 0.05 | + | 150 |
| 3 | PVA | 0.1 | + | 100 |
| 4 | HEC | 0.001 | + | 20 |
| 5 | HEC | 0.01 | ++ | 50 |
| 6 | HEC | 0.1 | ++ | 50 |
| 7 | MC | 0.05 | + | 50 |
| 8 | MC | 0.1 | ++ | 50 |
| 9 | MC | 0.15 | ++ | 100 |
| 10 | MHEC | 0.1 | ++ | 50 |
| 11 | HPC | 0.15 | ++ | 20 |
| 12 | MHPC | 0.15 | ++ | 20 |
| 13 | MHBC | 0.15 | ++ | 20 |
| 14 | CMC | 5.0 | ++ | 100 |
| 15 | CMMC | 0.15 | ++ | 50 |
| 16 | guar | 5.0 | + | 50 |
| 17 | PVA/MC(1:1) | 0.1 | + | 50 |
| 18 | PVA/HEC(1:1) | 0.1 | + | 50 |
| 19 | MC/HEC(1:1) | 0.1 | + | 50 |

TABLE 2

Rate of cooling: 20° C./hour

| experiment No. | additive | wt. % of additive | crystal form |
|---|---|---|---|
| 20 | MC | 0.05 | ++ |
| 21 | MHEC | 0.10 | + |
| 22 | HPC | 0.15 | + |
| 23 | HEC | 0.10 | ++ |
| 24 | MHBC | 0.05 | ++/+ |
| 25 | CMMC | 0.05 | ++ |
| 26 | PVA | 0.5 | ++ |

TABLE 3

Rate of cooling: 50° C./hour

| experiment No. | additive | wt. % of additive | crystal form |
|---|---|---|---|
| 27 | MC | 0.1 | ++/+ |
| 28 | MHEC | 0.1 | + |
| 29 | HEC | 0.1 | + |
| 30 | MHBC | 0.1 | ++/+ |
| 31 | CMMC | 0.1 | ++/+ |

We claim:

1. A process for the moification of the crystal form of dicyandiamide, comprising crystallizing the dicyandiamide from aqueous solution, in the presence of 0.001 to 10% by weight of polyvinyl alcohol, a water-soluble cellulose ether derivative, guar or a combination thereof, based on the weight of dicyandiamide, by cooling the aqueous solution.

2. Process according to claim 1, wherein the dicyandiamide is crystallised from aqueous solution in the presence of 0.05 to 5% by weight of polyvinyl alcohol, the water-soluble cellulose ether derivative, guar or combination thereof, based on the weight of dicyandiamide.

3. Process according to claim 1, wherein the water-soluble cellulose ether derivative is selected from non-ionic, mixed nonionic, ionic and ionic/nonionic cellulose ethers.

4. process according to claim 1, wherein the water-soluble cellulose ether derivative is methylcellulose, hydroxyethylcellulose, hydroxypropylcellulose, hydroxyethylcellulose, methylhydroxyethylcellulose, methylhydroxypropylcellulose, methylhydroxybutylcellulose, sodium carboxymethylcellulose or carboxymethylcellulose.

5. Process according to claim 1 wherein the polyvinyl alcohol is used in the form of partly saponified polyvinyl acetate.

6. Process according to claim 1 wherein a defoaming agent is added.

7. A process for the modification of the crystal form of dicyandiamide, comprising crystalizing the dicyandiamide from aqueous solution in the presence of 0.001 to 10% by weight of polyvinyl alcohol, a water-soluble cellulose ether derivative, guar or a combination thereof, based on the weight of dicyandiamide, wherein the crystallization is carried out with cooling and the rate of cooling during crystallization is 1° to 70° C. per hour.

8. Process according to claim 7, wherein the rate of cooling during crystallisation is 10° to 50° C. per hour.

9. Process according to claim 1 wherein the dicyandiamide is produced from an alkaline medium; the polyvinyl alcohol and/or water-soluble cellulose ether derivative being added during the production of the dicyandiamide in an alkaline medium.

10. Process according to claim 1 wherein the bulk density of the crystals obtained is 300 to 800 g./liter.

11. Process according to claim 10, wherein the bulk density of the crystals obtained is 500 to 700 g./liter.

* * * * *